(12) United States Patent
Fletcher et al.

(10) Patent No.: US 10,286,213 B2
(45) Date of Patent: May 14, 2019

(54) NEUROSTIMULATOR SYSTEM, APPARATUS, AND METHOD

(71) Applicant: AUTONOMIC TECHNOLOGIES, INC., Redwood City, CA (US)

(72) Inventors: Kellie Fletcher, Oakland, CA (US); Patrick Hard, Redwood City, CA (US); Anthony V. Caparso, San Francisco, CA (US); Karen Tsuei, Redwood City, CA (US)

(73) Assignee: AUTONOMIC TECHNOLOGIES, INC., Redwood City, CA (US)

( * ) Notice: Subject to any disclaimer, the term of this patent is extended or adjusted under 35 U.S.C. 154(b) by 115 days.

(21) Appl. No.: 15/362,124

(22) Filed: Nov. 28, 2016

(65) Prior Publication Data

US 2017/0072200 A1    Mar. 16, 2017

Related U.S. Application Data

(60) Division of application No. 14/801,211, filed on Jul. 16, 2015, now abandoned, which is a division of application No. 13/722,185, filed on Dec. 20, 2012, now abandoned, and a continuation-in-part of application No. 12/765,712, filed on Apr. 22, 2010, now Pat. No. 8,494,641, and a continuation-in-part of application No. 12/688,524, filed on Jan. 15, 2010, now Pat. No. 9,320,908.

(Continued)

(51) Int. Cl.
*A61N 1/05* (2006.01)
*A61N 1/36* (2006.01)
*A61N 1/372* (2006.01)
*A61N 1/375* (2006.01)
*A61N 1/378* (2006.01)

(52) U.S. Cl.
CPC ....... *A61N 1/36075* (2013.01); *A61N 1/0526* (2013.01); *A61N 1/0529* (2013.01); *A61N 1/0558* (2013.01); *A61N 1/36071* (2013.01); *A61N 1/36132* (2013.01); *A61N 1/375* (2013.01); *A61N 1/3787* (2013.01); *A61N 1/37235* (2013.01); *A61N 1/37241* (2013.01); *A61N 1/37247* (2013.01); *A61N 1/37264* (2013.01); *A61N 1/37282* (2013.01)

(58) Field of Classification Search
CPC ...... A61N 1/05; A61N 1/0526; A61N 1/0529; A61N 1/0558; A61N 1/36; A61N 1/36071; A61N 1/36075; A61N 1/372; A61N 1/37235; A61N 1/37241; A61N 1/37247; A61N 1/37282; A61N 1/385; A61N 1/3787
USPC .............................. 607/59, 60, 61
See application file for complete search history.

(56) References Cited

U.S. PATENT DOCUMENTS

5,749,909 A    5/1998  Schroeppel
6,526,318 B1   2/2003  Ansarinia
(Continued)

*Primary Examiner* — Christopher A Flory
(74) *Attorney, Agent, or Firm* — Tarolli, Sundheim, Covell & Tummino LLP (57) ABSTRACT

An apparatus (10) for applying stimulation therapy to a patient includes an implantable medical device (20) and a remote controller (50) for inductively powering the medical device and communicating with the medical device. The remote controller (50) includes a feedback portion (220) for helping to establish a communication link between the remote controller and the implantable medical device (20).

17 Claims, 7 Drawing Sheets

Related U.S. Application Data (60) Provisional application No. 61/578,415, filed on Dec. 21, 2011, provisional application No. 61/177,895, filed on May 13, 2009, provisional application No. 61/171,749, filed on Apr. 22, 2009, provisional application No. 61/145,003, filed on Jan. 15, 2009.

(56) References Cited

U.S. PATENT DOCUMENTS

| | | |
|---|---|---|
| 6,735,475 B1 | 5/2004 | Whitehurst |
| 7,561,919 B2 | 7/2009 | Shalev |
| 8,005,539 B2 | 8/2011 | Burnes |
| 8,055,347 B2 | 11/2011 | Lamensdorf |
| 8,165,691 B2 | 4/2012 | Ellingson |
| 8,209,028 B2 | 6/2012 | Skelton |
| 8,473,062 B2 | 6/2013 | Pless |
| 8,494,641 B2 | 7/2013 | Boling |
| 8,886,325 B2 | 11/2014 | Boling |
| 2002/0073334 A1 | 6/2002 | Sherman |
| 2003/0018368 A1 | 1/2003 | Ansarinia |
| 2003/0176892 A1 | 9/2003 | Shalev |
| 2003/0176898 A1 | 9/2003 | Gross |
| 2004/0015068 A1 | 1/2004 | Shalev |
| 2004/0210269 A1 | 10/2004 | Shalev |
| 2005/0153885 A1 | 7/2005 | Yun |
| 2005/0159790 A1 | 7/2005 | Shalev |
| 2005/0209654 A1 | 9/2005 | Boveja |
| 2005/0266099 A1 | 12/2005 | Shalev |
| 2006/0009815 A1 | 1/2006 | Boveja |
| 2006/0079936 A1 | 4/2006 | Boveja |
| 2006/0111754 A1 | 5/2006 | Rezai |
| 2006/0129205 A1 | 6/2006 | Boveja |
| 2006/0173259 A1 | 8/2006 | Flaherty |
| 2006/0217782 A1 | 9/2006 | Boveja |
| 2006/0276854 A1 | 12/2006 | Shalev |
| 2006/0287678 A1 | 12/2006 | Shafer |
| 2007/0067004 A1 | 3/2007 | Boveja |
| 2007/0083245 A1 | 4/2007 | Lamensdorf |
| 2007/0142875 A1 | 6/2007 | Shalev |
| 2007/0250119 A1 | 10/2007 | Tyler |
| 2008/0021341 A1 | 1/2008 | Harris |
| 2008/0021503 A1* | 1/2008 | Whitehurst ........ A61M 5/14276 607/3 |
| 2008/0033509 A1 | 2/2008 | Shalev |
| 2008/0172102 A1 | 7/2008 | Shalev |
| 2008/0208280 A1* | 8/2008 | Lindenthaler ........ A61B 5/4836 607/42 |
| 2008/0221921 A1 | 9/2008 | Love |
| 2009/0024189 A1* | 1/2009 | Lee .................... A61N 1/36017 607/66 |
| 2009/0105783 A1 | 4/2009 | Solberg |
| 2009/0276005 A1* | 11/2009 | Pless .................... A61N 1/08 607/46 |
| 2009/0312617 A1 | 12/2009 | Hogle et al. |
| 2009/0312817 A1 | 12/2009 | Hogle |
| 2010/0010586 A1 | 1/2010 | Skelton |
| 2010/0143413 A1 | 6/2010 | Papay |
| 2010/0179617 A1 | 7/2010 | Fletcher |
| 2010/0222845 A1 | 9/2010 | Goetz |
| 2010/0228314 A1 | 9/2010 | Goetz |
| 2010/0274313 A1 | 10/2010 | Boling |
| 2011/0015693 A1 | 1/2011 | Williamson |
| 2011/0125214 A1 | 5/2011 | Goetz |
| 2011/0125215 A1 | 5/2011 | Goetz |
| 2011/0184494 A1 | 7/2011 | Shalev |
| 2011/0313487 A1* | 12/2011 | Kokones ................ G16H 50/50 607/59 |
| 2012/0150255 A1* | 6/2012 | Lindenthaler ........ A61N 1/0553 607/42 |
| 2012/0302912 A1 | 11/2012 | Moffitt |
| 2013/0110195 A1 | 5/2013 | Fletcher |
| 2013/0116745 A1 | 5/2013 | Fletcher |
| 2013/0296993 A1 | 11/2013 | Boling |
| 2014/0207220 A1 | 7/2014 | Boling |
| 2015/0142082 A1* | 5/2015 | Simon ................ A61N 1/36053 607/61 |
| 2015/0174406 A1* | 6/2015 | Lamensdorf ........ A61N 1/36057 607/62 |
| 2015/0258338 A1 | 9/2015 | Kishawi |
| 2016/0001079 A1 | 1/2016 | Fletcher |
| 2016/0008608 A1 | 1/2016 | Boling |

\* cited by examiner

NEUROSTIMULATOR SYSTEM, APPARATUS, AND METHOD

RELATED APPLICATIONS

This application is a divisional of U.S. patent application Ser. No. 14/801,211, filed on Jul. 16, 2015, which is a divisional of U.S. patent application Ser. No. 13/722,185, filed on Dec. 20, 2012, which claims the benefit of U.S. Provisional Application No. 61/578,415, filed Dec. 21, 2011. U.S. patent application Ser. No. 13/722,185 is a continuation-in-part of U.S. patent application Ser. No. 12/688,524, filed Jan. 15, 2010, now issued as U.S. Pat. No. 9,320,908, issued Apr. 26, 2016, titled "APPROVAL PER USE IMPLANTED NEUROSTIMULATOR," which claims the benefit of U.S. Provisional Application No. 61/145,003 filed Jan. 15, 2009. U.S. patent application Ser. No. 13/722,185 is also a continuation-in-part of U.S. patent application Ser. No. 12/765,712, filed Apr. 22, 2010, now issued as U.S. Pat. No. 8,494,641, issued Jul. 23, 2013, titled "IMPLANTABLE NEUROSTIMULATOR WITH INTEGRAL HERMETIC ELECTRONIC ENCLOSURE, CIRCUIT SUBSTRATE, MONOLYTHIC FEED-THROUGH, LEAD ASSEMBLY AND ANCHORING MECHANISM," which claims the benefit of U.S. Provisional Application No. 61/171,749 filed Apr. 22, 2009, and U.S. Provisional Application No. 61/177,895 filed May 13, 2009. The full disclosures of these applications are hereby incorporated by reference in their entirety.

FIELD OF THE INVENTION

The invention relates generally to systems, devices, and methods for using an implantable medical device to deliver therapy to a patient. More specifically, according to one aspect of the invention, systems, devices, and methods according to the invention are used to deliver electrical stimulation to a peripheral, central or autonomic neural structure. In one particular aspect, the invention relates to neurostimulator systems, devices, and methods for treating primary headaches, such as migraines, cluster headaches, trigeminal autonomic cephalalgias and/or many other neurological disorders, such as atypical facial pain and/or trigeminal neuralgias.

BACKGROUND OF THE INVENTION

Primary headaches are debilitating ailments that afflict millions of individuals worldwide. The specific pathophysiology of primary headaches is not known. Known causes of headache pain include trauma, vascular defects, autoimmune deficiencies, degenerative conditions, infections, drug and medication-induced causes, inflammation, neoplastic conditions, metabolic-endocrine conditions, iatrogenic conditions, musculoskeletal conditions, and myofacial causes. In many situations, however, even though the underlying cause of the headache may be identified and treated, the headache pain itself may persist.

Recent clinical studies in treatment of headaches have targeted the manipulation of sphenopalatine (pterygopalatine) ganglion (SPG), a large, extra cranial parasympathetic ganglion. A ganglion is a mass of nervous tissue found in some peripheral and autonomic nerves. Ganglia are located on the roots of the spinal nerves and on the roots of the trigeminal nerve. Ganglia are also located on the facial, glossopharyngeal, vagus and vestibulochoclear nerves. The SPG is a complex neural ganglion with multiple connections, including autonomic, sensory, and motor connections. The SPG includes parasympathetic neurons that innervate, in part, the middle cerebral and anterior cerebral blood vessels, the facial blood vessels, and the lacrimal glands.

The maxillary branch of the trigeminal nerve and the nerve of the pterygoid canal (also known as the vidian nerve which is formed by the greater and deep petrosal nerves) send neural projections to the SPG. The fine branches from the maxillary nerve (pterygopalatine nerves) form the sensory component of the SPG. These nerve fibers pass through the SPG and do not synapse. The greater petrosal nerve carries the preganglionic parasympathetic axons from the superior salivary nucleus, located in the Pons, to the SPG. These fibers synapse onto the postganglionic neurons within the SPG. The deep petrosal nerve connects the superior cervical sympathetic ganglion to the SPG and carries postganglionic sympathetic axons that again pass through the SPG without any synapses.

The SPG is located within the pterygopalatine fossa. The pterygopalatine fossa is bounded anteriorly by the maxilla, posteriorly by the medial plate of the pterygoid process and greater wing of the sphenoid process, medially by the palatine bone, and superiorly by the body of the sphenoid process. The lateral border of the pterygopalatine fossa is the pterygomaxillary fissure, which opens to the infratemporal fossa.

Various clinical approaches have been used to modulate the function of the SPG in order to treat headaches, such as cluster headaches or chronic migraines. These approaches vary from lesser or minimally invasive procedures (e.g., transnasal anesthetic blocks) to procedures or greater invasiveness (e.g., surgical ganglionectomy). Other procedures of varying invasiveness include those such as surgical anesthetic injections, ablations, gamma knife procedures, and cryogenic surgery. Although most of these procedures can exhibit some short term efficacy in the order of days to months, the results are usually temporary and the headache pain eventually reoccurs.

SUMMARY OF THE INVENTION

The invention relates to systems, devices, and methods for using an implantable medical device ("IMD") to deliver therapy to a patient. According to one aspect, the invention relates to an IMD for delivering electrical stimulation to a peripheral, central or autonomic neural structure. In this aspect, the IMD may comprise a neurostimulator for treating primary headaches, such as migraines, cluster headaches, trigeminal autonomic cephalalgias and/or many other neurological disorders, such as atypical facial pain and/or trigeminal neuralgias.

In one embodiment, an IMD and an associated handheld remote controller ("RC") each may have an operating memory for storing a programmable operating instructions and data, both input and recorded, that govern the operation of each respective device. The IMD and RC each may also include processing hardware, associated with the operating memory, for executing the programmable operating instructions in accordance with the input and recorded data. According to one aspect, the IMD may receive from the RC operating instructions, data, or both operating instructions and data, that at least partially govern the therapies applied via the IMD. The governed therapies may include either or both therapies delivered within a clinical trial and a post-market usage.

The IMD administers therapy in accordance with stimulation parameters stored on the IMD. The stimulation parameters may be programmed into the IMD in a variety of manners. For example, the stimulation parameters may be programmed via a programming system, which can be either local to or remote from the device. Local programming of the IMD can be accomplished, for example, with the patient near a physician's workstation, which can communicate wirelessly with the device (e.g., via Bluetooth, long range induction, etc.) or with the RC acting as an interface or wand to the device. Remote programming of the IMD can be accomplished by establishing communication with the RC via one or more communication networks. For example, a remotely located physician's workstation can communicate with a patient's personal computer via an internet connection, which relays the stimulation parameters to the IMD via the RC acting as an interface.

According to another aspect of the invention, the RC is configured to prompt for and elicit from the patient subjective and objective data, which the patient enters via the RC. The RC records the patient input data, and also records data associated with the treatment applied by the IMD. The data can then be transmitted to the physician's workstation or possibly mobile device such as a PDA, cell phone, tablet, etc., so that the physician can use the data to verify the stimulation parameters for current therapy or to determine control or stimulation parameter adjustments for subsequent therapies or determine if the current stimulation parameters provide effective therapy to the patient.

Accordingly, the present invention relates to an apparatus for applying stimulation therapy to a patient includes an implantable medical device and a remote controller for inductively powering the medical device and communicating with the medical device. The remote controller includes a feedback portion for helping to establish a communication link between the remote controller and the implantable medical device, answering patient subjective and objective data, and other system alerts.

The invention also relates to a method for coupling a remote controller to an implantable medical device. The method includes the steps of positioning the remote controller relative to the medical device. The method also includes the step of adjusting the position of the remote controller relative to the medical device in response to an optimal communication feedback provided by the remote controller. The method includes the further step of maintaining the position of the remote controller in response to a communication maintenance feedback provided by the remote controller.

The invention also relates to an apparatus for applying stimulation therapy to a patient. The apparatus includes an implantable medical device storing at least one of stimulation parameters and therapy settings and a remote controller for inductively powering the medical device. The medical device is adapted to apply stimulation therapy to the patient according to the stimulation parameters and therapy settings.

The invention further relates to a method for applying stimulation therapy to a patient. The method includes the step of implanting an implantable medical device in the patient. The method also includes the step of storing at least one of stimulation parameters and therapy settings on the medical device. The method also includes the step of using a remote controller to inductively power the implanted medical device. The method includes the further step of applying via the implanted medical device stimulation therapy to the patient according to the stimulation parameters and therapy settings.

BRIEF DESCRIPTION OF THE DRAWINGS

FIGS. 5-7B are functional block diagrams illustrating various steps in a process that can be performed by the medical device of FIG. 1, according to the invention.

DESCRIPTION OF THE PREFERRED EMBODIMENTS

The invention relates to systems, devices, and methods for imparting a therapy on a patient. More particularly, the invention relates to devices, systems, and methods for applying patient stimulation therapies a patient. According to one aspect of the invention, the devices, systems, and methods of the invention provide for feedback to the patient that helps to improve the effectiveness of the stimulation therapy.

Figure 1:
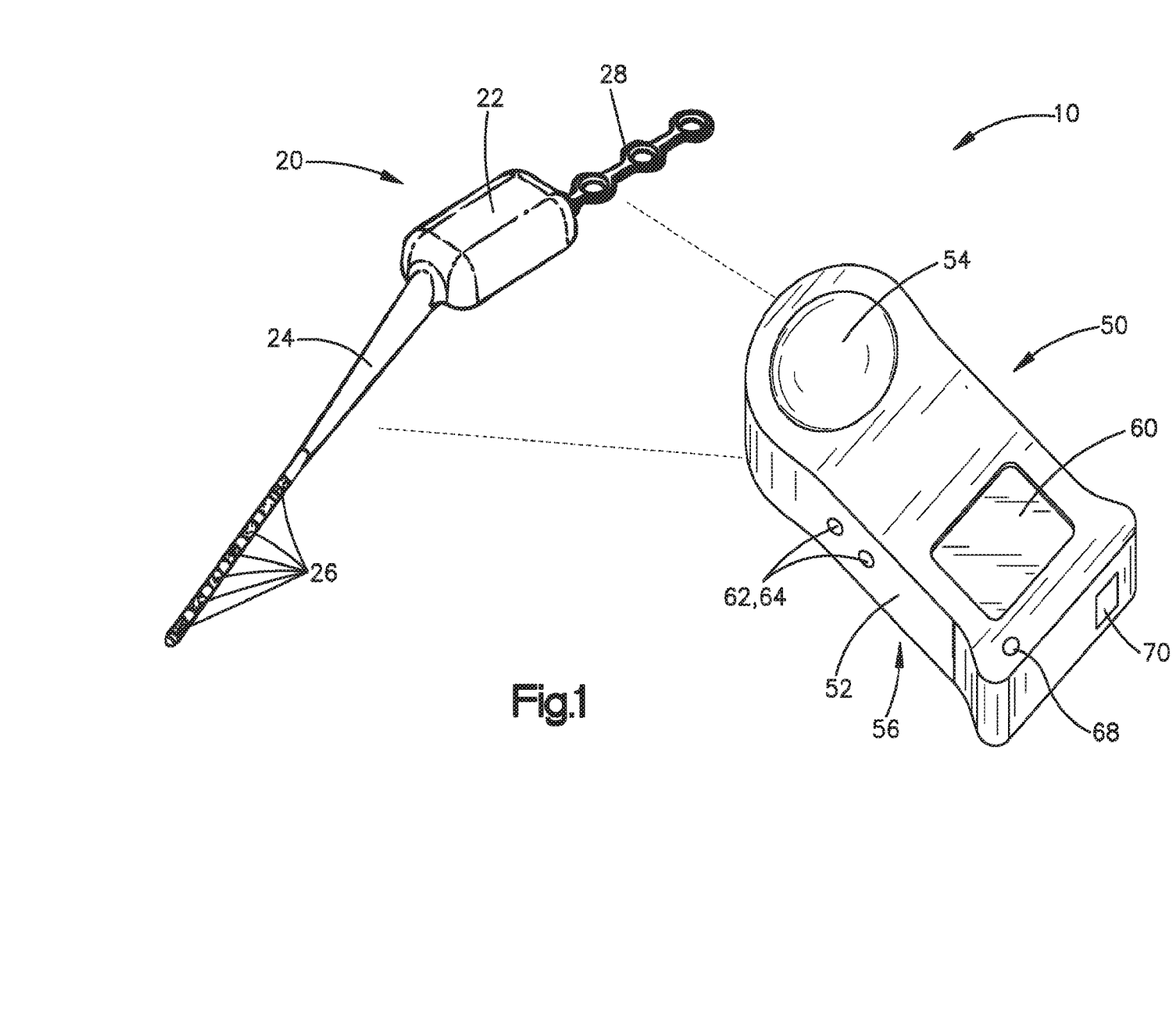
FIG. 1 is a schematic illustration of devices that form a portion of a system for delivering therapy using an implantable medical device, according to the invention.

FIG. 1 illustrates by way of example a medical device forming a portion of a system that can be implemented in accordance with the invention. Referring to FIG. 1, according to one aspect of the invention, a medical device 10 includes an implantable medical device ("IMD") 20 and a handheld remote controller ("RC") 50 for interfacing with and controlling operation of the IMD. In this description, the term "implantable" is meant to describe that the medical device is configured for in vivo placement in the patient by surgical or other means. In the illustrated embodiment, the IMD 20 is shown and described as an implantable neurostimulator. The IMD 20 may, for example, be a neurostimulator of the type shown and described in co-pending U.S. Patent Application Publication No. US 2010/027413 A1, the disclosure of which is hereby incorporated by reference in its entirety.

The neurostimulator embodying the IMD 20 illustrated and described herein is an example of just one particular IMD that may be implemented in accordance with the systems, devices, and methods of the invention. Those skilled in the art will appreciate that the systems, devices, and methods of the invention can be applied to implantable stimulators other than the neurostimulator illustrated in FIG. 1 without departing from the spirit of the invention. Those skilled in the art will also appreciate that the systems, devices, and methods of the invention can be applied to IMDs other than stimulators, in general, and other than neurostimulators, more specifically.

The IMD 20 illustrated in FIG. 1 includes a stimulator body 22, a stimulator lead 24 including one or more stimulating electrodes 26, and an anchoring portion 28. The IMD 20 is an inductively powered system having stored programmed stimulation parameters and bi-directional telemetry to facilitate communication between the implanted device and the external RC 50. The body 22 comprises an electronics enclosure that can house, for example, an application-specific integrated circuit, various passive components, and an antenna/coil for radio frequency transfer of power and communication. The lead 24 provides an electrical connection between the electronics housed in the body portion 22 and the stimulating electrodes 26. Each of the one or more electrodes 26 provides a site for electrical stimulation of the target anatomy.

The IMD 20 of the example embodiment of FIG. 1 is powered inductively by the RC 50 and has electronics, micro-electronic components, and integrated circuits necessary to store settings, parameters, and other data. During a therapy session, the IMD 20, powered by the RC 50, delivers electrical stimulation per the stimulation parameters stored on the IMD. Each of the electrodes 26 is controllable independently, which allows the physician to select which electrodes will serve as anodes and which electrodes will serve as cathodes in any combination. The IMD 20 can apply the stimulation therapy in accordance with the stimulation parameters stored on the IMD. Additionally, the IMD 20 can acquire and transmit to the RC 50 therapy session data gathered during a therapy session. The IMD 20 includes a non-volatile memory for storing the stimulation parameters and other clinical trial related information.

The RC 50 provides inductive power to the IMD 20 and communicates (e.g., via radio frequency) with the IMD. Through this communication, the RC 50 can access settings and parameters stored on the IMD 20 and also record therapy session data (in real-time or at a predetermined time). For example, in an embodiment used in a clinical trial, the RC 50 may record therapy session data in real time while also accessing clinical trial specific data (e.g., trial type, specific questions to be asked, therapy randomization strings, language settings, etc.) in real-time or at some predetermined time before, during, or after the therapy session. In another example, in an embodiment used in a post-market patient usage, the RC 50 may record therapy session data in real time while also recording post-market specific data (e.g., specific questions to be asked) in real-time or at some predetermined time before, during, or after the therapy session.

Also, in this description, reference is made to stimulation parameters that may be programmed and/or stored on the IMD 20 and accessed and transmitted to/from the RC 50. The term "stimulation parameters," as used herein, is meant to encompass the parameters that define the stimulation therapy applied to the patient by the medical device 10. In a clinical trial setting, the stimulation parameters may include parameters for each of several therapy modes or configurations used during the clinical trial. The stimulation parameters include, but are not limited to, the parameters set forth below in Table 1:

TABLE 1

Stimulation Parameters

Amplitude
Frequency
Pulse Width
Pulse Interval
Electrode Settings
Patient Limits
Amplitude Ramp Rates
Pulse Width Ramp Rates
Biphasic or Monophasic Stimulation Pulses Additionally, in this description, reference will be made to therapy settings programmed and/or stored on the IMD 20 and accessed and transmitted to/from the RC 50. The term "therapy settings," as used herein, is meant to refer to patient specific settings and data that customize the medical device 10 according to patient needs/preferences and physician/clinician requirements. The therapy settings include, but are not limited to, the settings set forth below in Table 2:

TABLE 2

Therapy Settings

Language Preference
Screen Brightness, Color, etc.
Screen Appearance/Fonts
Text Size
Patient Preferred Feedback Modes
Volume
Patient Diary Questions
Diary Date/Time Schedule
Patient Diary Entries
Diary Dates/Times
Hardware Identification/Ser. No.

Additionally, in this description, reference will be made to therapy session data that can be recorded, stored and transmitted by the RC 50. The term "therapy session data," as used herein, is meant to refer to data related to the therapy applied by the medical device 10 during a session. The therapy session data includes, but is not limited to, the data set forth below in Table 3:

TABLE 3

Therapy Session Data

Electrode Impedances
Electrode Opens/Shorts
Date/Time of Therapy Start
Date/Time of Therapy End
Therapy Session Duration
Manual Patient Adjustments
Patient Attempted djustments
Ramp Times
Maximum Amplitude
Actual Amplitudes
Time at Each Setting
Patient Diary Entries
Diary Dates/Times
Software/Firmware Versions
Serial Number Data
Data Integrity Check Data
IMD Register Values
Tilt/Fault Data
Communication Loss Data Referring to FIG. 1, the RC 50 includes a body portion 52 and an antenna portion 54. The body portion 52 is ergonomically shaped/contoured and includes a graphical user interface ("GUI") 56 that includes a display 60 and a user navigation/input controls 62. The display 60 may, for example, comprise an LED or LCD display, color or B&W, that displays the status, settings, and other data related to the operation of the RC 50. The RC 50 interface 56 may be fully customizable, i.e., the color, brightness, font, text size, sound volume, etc. can be adjusted to suit the patient. The user navigation/input device 62 illustrated in FIG. 1 comprises control buttons 64 that are located at an ergonomic position on the RC 50 so that they can be accessed with either right or left hand while the controller is held in the therapy position. The user navigation/input device 62 could, however, comprise alternative devices, such as a touch screen, track ball, touch pad, thumb wheel, etc. The navigation/input device 62 may also be customizable in that the buttons and other devices may have functions that are programmable or assignable by the user.

The RC 50 also includes a power button 68 and I/O ports in the form of a USB/charging port 70. The RC 50 may include multiple ports and other connectivity features for providing flexibility in communications, data transfer, software/firmware uploading/downloading. Such additional ports may also be used to provide for connectivity and expandability with peripheral devices, such as a Bluetooth or other add-on communications module, or a remote inductive coil device.

The RC 50 includes a power source that includes batteries (disposable or rechargeable) and may also be powered externally via a cable connection (e.g., via AC outlet or USB). The antenna portion 54 includes a coil for inductively powering the IMD 20 and for communicating with the IMD. The RC 50 is configured to power and communicate with the IMD 20 when the RC 50 is brought into a predefined proximity (e.g., within 5 centimeters) of the IMD.

The RC 50 is illustrative of one example controller that may be implemented in accordance with the systems, apparatuses, and methods of the invention. Those skilled in the art will appreciate that certain aspects of the systems, apparatuses, and methods of the invention can be applied to controllers other than the RC 50 illustrated in FIG. 1 without departing from the spirit of the invention.

Figure 4:
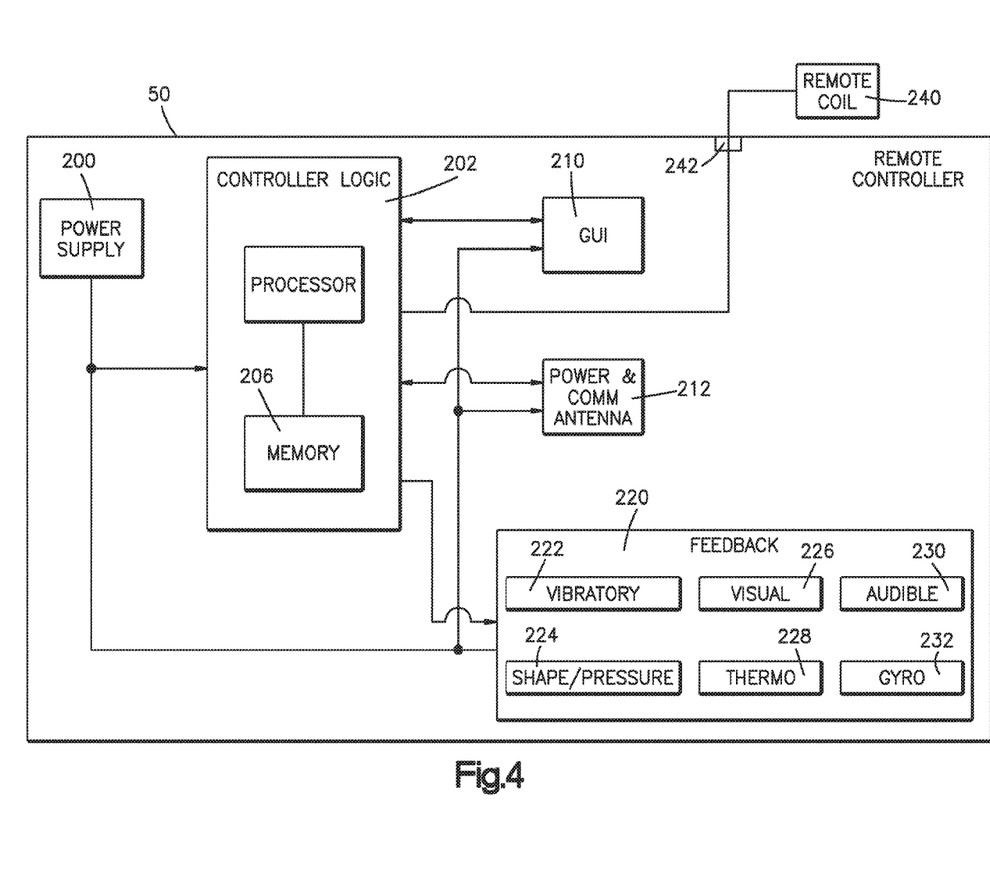
FIG. 4 is a schematic block diagram of a portion of the system of FIG. 3, according to the invention.

For example, FIG. 4 illustrates one possible internal configuration of the RC 50. The configuration illustrated in FIG. 4 is an example configuration that shows certain components that may be employed by the RC 50. Those skilled in the art will appreciate that the configuration illustrated in FIG. 4 is but one of many example configurations of components that may be implemented in the RC 50. Components may be added, omitted or may be arranged differently than shown in FIG. 4 without departing from the spirit of the invention.

Referring to FIG. 4, the RC 50 includes a power supply 200 and a controller logic portion 202. The controller logic portion 202 includes one or more processors 204 (e.g., microprocessors, ASICs, etc.) and a memory portion 206 (e.g., non-volatile memory). The logic portion 202 controls the operation of the RC 50 according to programmed instructions and data or other parameters that are programmed onto or retrieved from the IMD 20.

The RC 50 also includes a graphical user interface ("GUI") 210, which may comprise the input buttons 62, 64 and display screen 60 described above, along with any associated electronics, such as graphics drivers, input buffers, etc. The RC 50 also includes a power and communication antenna 212 that, as the name implies, includes the antenna(s) necessary to power the IMD 20 and communicate with the IMD.

The power supply 200 may, for example, comprise a chargeable battery system with conventional AC wall power being available to charge the batteries or power the device directly. The power supply 200 supplies power to the controller logic portion 202, the GUI 210, and the power/communication antenna 212. The power supply 200 may power these components directly or indirectly via another component.

The RC 50 may also include a remote antenna 240, which may be an optional component that can be added as an accessory to the RC. The remote antenna 240 is a power/communication antenna that may be similar or identical to the antenna 212. The remote antenna 240 can be connected to the RC 50, for example, via a cable that plugs into socket 242. The remote antenna 240 would thus be powered by the power supply 200 of the RC 50.

In use, to establish communication between the RC 50 and the IMD 20, the antenna portion 54 of the RC 50 needs to be positioned within a certain distance of the IMD (e.g., within 5 centimeters). Additionally, the position of the RC 50 and, more particularly, the antenna portion 54 (i.e., direction, angle, etc.) can also affect the strength of the communication between the RC 50 and the IMD 20.

According to the invention, the RC 50 also includes a feedback portion 220 that provides feedback to the user for establishing and maintaining the communication link between the RC 50 and IMD 20 when applying stimulation therapy using the medical device 10. One particular feature of the feedback portion 220 is that it provides an indication to the patient that the RC 50 is in the proper or optimal position relative to the implanted IMD 20 for powering and communicating with the IMD. The feedback portion 220 may have other uses, such as indicating that the RC 50 is powered up, that a therapy session has ended, other alerts (for example that more therapy session need to be purchased or approved before using the RC again or contact your doctor) or to alert the patient of an error or loss of communication.

The feedback portion 220 may incorporate one or more modes for providing feedback to the patient. For example, as shown in FIG. 4, the feedback portion 220 may include vibratory feedback 222, visual feedback 226, audible feedback 230, shape/pressure feedback 224, thermal feedback 228, and gyroscopic feedback 232. The feedback provided by the various feedback modes are perceptible to the patient via one or more senses (e.g., sight, touch, hearing). Each feedback mode has one or more characteristics that change or adjust in response to conditions (e.g., communication signal strength, RC/IMD relative positions, etc.) that are indicated by the feedback. For example, in providing the feedback, the feedback mode characteristic(s) can be changed in response to the amount of data exchanged between the RC 50 and the IMD 20, which can be associated with the communication signal strength between the RC and the IMD. Additionally, or alternatively, parameters such as receiving antenna coil voltage at the RC 50 or IMD 20 can be measured, and the RC can adjust the feedback mode characteristic(s) in response to this measurement. Also, the feedback modes can be used in an "alarm clock" or "alert" mode to alert the patient of occurrences, such as software/firmware updates, stimulation parameter/therapy setting updates, diary entries/requirements, scheduled therapy, or even appointments, scheduling, etc. These feedback mode features may be available at any time the RC 50 is in communication with the network 170, either wired or wirelessly.

The vibratory feedback 222 may comprise a vibration motor that has either a fixed or a variable speed configuration. The vibratory feedback 222 can be throttled in response to the sensed relative position of the RC 50 and the IMD 20 by adjusting the speed of the vibration motor, e.g., by throttling motor voltage or via pulse width modulation. This throttling results in a corresponding change in the frequency of the vibration that can be sensed by the patient by touch, e.g., with the hand that is holding the RC 50 in the position of FIG. 2B. For example, in providing the vibratory feedback, the speed of the vibration motor can be changed in response to the communication signal strength between the RC 50 and the IMD 20, which can be determined as a function of the amount of data exchanged between the RC and the IMD, or as a function of the receiving antenna coil voltage of the RC or IMD.

The visual feedback 226 may comprise one or more light indicators (e.g., LEDs) on the RC 50 or a portion of the display screen 60. The visual feedback 226 can be throttled in response to the sensed relative position of the RC 50 and the IMD 20 by adjusting the intensity of the light indicators, the number of lights illuminated, or via a graphical display on the screen 60. The visual feedback 226, of course, requires sight by the patient while the RC is held in the patient's hand as shown in FIG. 2B. For example, in providing the visual feedback, LED brightness, LED numbers, and/or a visual display on the screen 60 can be changed in response to the communication signal strength between the RC 50 and the IMD 20, which can be determined as a function of the amount of data exchanged between the RC and the IMD, or as a function of the receiving antenna coil voltage of the RC or IMD.

The audible feedback 230 may comprise one or more audible indicators (e.g., speakers) on the RC 50. The audible feedback 230 can be throttled in response to the sensed relative position of the RC 50 and the IMD 20 by adjusting the volume, tone, pitch, etc. of the audible indicator. The audible feedback 230 can also incorporate recorded verbal feedback or instructions for achieving the optimal relative positions of the EC 50 and IMD 20. The audible feedback 230 does not require sight by the patient while the RC is held in the patient's hand as shown in FIG. 2B. For example, in providing the audible feedback, the volume, tone, pitch, etc. of the audible indicator can be changed in response to the communication signal strength between the RC 50 and the IMD 20, which can be determined as a function of the amount of data exchanged between the RC and the IMD, or as a function of the receiving antenna coil voltage of the RC or IMD.

The shape/pressure feedback 224 may comprise one or more piezoelectric, dielectric, shape memory alloy, or slow actuators that can change or alter their shape. The shape/pressure feedback 224 can be throttled, or the position of the pressure/shape change can be moved in response to the sensed relative position of the RC 50 and the IMD 20. The shape/pressure feedback 224 does not require sight by the patient while the RC is held in the patient's hand as shown in FIG. 2B. For example, in providing the shape/pressure feedback, the shape/pressure feedback 224 can be adjusted in magnitude or location in response to the communication signal strength between the RC 50 and the IMD 20, which can be determined as a function of the amount of data exchanged between the RC and the IMD, or as a function of the receiving antenna coil voltage of the RC or IMD.

The thermal feedback 228 may comprise one or more thermoelectric elements, such as peltier elements, that can change temperature. The thermal feedback 228 can be throttled in response to the sensed relative position of the RC 50 and the IMD 20 by adjusting the applied current/voltage. The temperature feedback 228 does not require sight by the patient while the RC is held in the patient's hand as shown in FIG. 2B. For example, in providing the thermal feedback, the temperature can be changed in response to the communication signal strength between the RC 50 and the IMD 20, which can be determined as a function of the amount of data exchanged between the RC and the IMD, or as a function of the receiving antenna coil voltage of the RC or IMD.

The gyroscopic feedback 232 may comprise one or more electronic gyroscopes that can stabilize the position and position of the RC 50 once the communication is achieved. The gyroscopic feedback 232 can be used to help maintain the optimal relative positioning between the RC 50 and IMD 20 once achieved. For example, the gyroscopic feedback 232 can be tied to the audible or visual feedbacks 230, 226 and can use them to provide instruction for maintaining the achieved optimal position. While the gyroscopic feedback 232 does not require sight by the patient while the RC is held in the patient's hand as shown in FIG. 2B, the other feedbacks used in conjunction may require sight. The gyroscopic feedback 232 could have additional uses. For example, the gyroscopic feedback 232 could be used to "memorize" an optimal position relative to the IMD 20 and could be used in conjunction with another of the feedback modes (e.g., audible, vibration, visual, etc.) to help guide the user to the optimal communication position.

One of the primary functions of the feedback portion 220 is to provide feedback on the proper positioning of the power/communication antenna 212 relative to the IMD 20. To do this, each of the feedback modes has one or more characteristics that adjust or change in magnitude in response to the position of the RC 50 relative to the IMD 20. In addition to this, each of the feedback modes may employ an additional indicator that signals when the optimal positioning of the RC 50 and IMD 20 are achieved, and when that optimal positioning is lost. The feedback modes may be employed individually or in combination with each other, and may be selectable and configurable to a patient/physician preference.

The primary feedback modes for establishing optimal communication between the RC 50 and IMD 20 are the vibratory feedback 22, the visual feedback 226, and the audible feedback 230. Once the optimal communication feedback is established, the feedback modes can provide feedback indicating whether the optimal communication is maintained and how to position/reposition the RC 50 to maintain the optimal communication. This communication maintenance feedback can be provided by any of the feedback modes. The optimal communication feedback and the communication maintenance feedback can be communicated using the same or different feedback modes. For the purpose of providing clarity to the patient, those skilled in the art will appreciate that it may be desirable to use different feedback modes for these functions.

For example, the vibratory feedback 222 may be used to provide the optimal communication feedback and the audible feedback 230 may be used to provide the communication maintenance feedback. In this configuration, the vibration feedback 222 may increase or decrease in frequency as the relative positions are adjusted, with a higher frequency being indicative of better features that help guide the patient toward the optimal RC position. When the optimal relative positions are achieved, the audible feedback 230 may provide an audible indication. Thereafter, the audible feedback 230 may provide additional audible indication for maintaining the optimal communication position.

As another example, the audible feedback 230 and/or the visual feedback 226 may be used to provide the optimal communication feedback and the communication maintenance feedback. In this configuration, the audible feedback 230 may increase or decrease in tone, volume, frequency, etc. as the relative positions are adjusted, and the visual feedback 226 may increase in intensity, brightness, number of lights as the relative positions are adjusted. When the optimal relative positions are achieved, the audible feedback 230 may provide an audible indication. Thereafter, the audible feedback 230 and/or the visual feedback 226 may provide additional audible indication for maintaining the optimal communication position.

As a further example, any of the vibratory feedback 222, the audible feedback 230, and the visual feedback 226 may be used to provide the optimal communication feedback and the gyroscopic feedback 232, in combination with the audible feedback 230, may be used to provide the communication maintenance feedback. Once the optimal relative positions are achieved and the optimal communication feedback indication is issued, the gyroscopic feedback 230 may store or "memorize" the position or position of the RC 50. Thereafter, the gyroscopic feedback 230 may, via the audible feedback 230, provide the communication maintenance feedback. In doing so, the audible feedback 230 may be in the form of an audible beep or tone, or even can be voice commands instructing the patient on where to move the RC 50.

Additionally, during use of the remote antenna, the feedback portion 220, particularly the visual feedback 226, can become advantageous. This is because the antenna 240, being remote from the RC 50 allows the patient to clearly view the display screen 60 while holding the remote antenna in against the his/her head.

Advantageously, the feedback portion 220 of the RC 50 helps guide the patient to the optimal communication position of the RC 50 relative to the IMD 20. According to the invention, the vibratory feedback 222 can be of a particular advantage in the embodiment illustrated in FIGS. 2A and 2B since, in use, the RC 50 is held by the patient in a position where visual feedback may be difficult or impossible. Additionally, since the feedback may include both optimal communication feedback and communication maintenance feedback, it is advantageous that the RC 50 includes two feedback modes (e.g., vibratory and audible) that can be used to differentiate between the two types of feedback.

The feedback portion 220 of the RC 50 may provide additional enhancements to either or both the optimal communication feedback and communication maintenance feedback. For example, the feedback portion 220 may include surface texturing, vibrations, or thermal feedback that is distributed to different locations on the RC 50. These distributed feedback modes can provide direction to the patient on how or in which direction to adjust the position of the RC 50 in order to achieve optimal communication. For instance, the feedback modes could be distributed to locations where the patient would normally rest their palms or fingers on the RC 50 or, additionally or alternatively, where the RC rests on the patient's face during use. These distributed feedback modes can serve as the optimal communication feedback and/or the communication maintenance feedback in order to help direct the patient to and maintain the optimal communication position.

In operation, the RC 50 transfers energy to the IMD 20 via near field electromagnetic induction. The RC 50 transmits power signals via the power antenna, located in the antenna portion 54, at a specific frequency. The IMD 20 includes a power coil/antenna that is tuned to resonate close to the frequency at which the RC 50 transmits the power signal and thereby generates, through induction, power for the IMD.

The RC 50 also communicates with the IMD 20 to provide, for example, stimulation parameters, software/firmware upgrades, and other operating instructions and data prior to or subsequent to IMD implantation. The RC 50 may also receive from the IMD 20 therapy session data, handshaking communications, and current stimulation parameter settings.

The antenna(s) employed in the antenna portion 54 of the RC 50 may have various designs. For example, the antenna portion 54 may include a first antenna for inductively powering the IMD 20 and for transmitting communications to the IMD. The antenna portion 54 may also include a second antenna for receiving communication transmissions from the IMD 20.

Figure 2A:
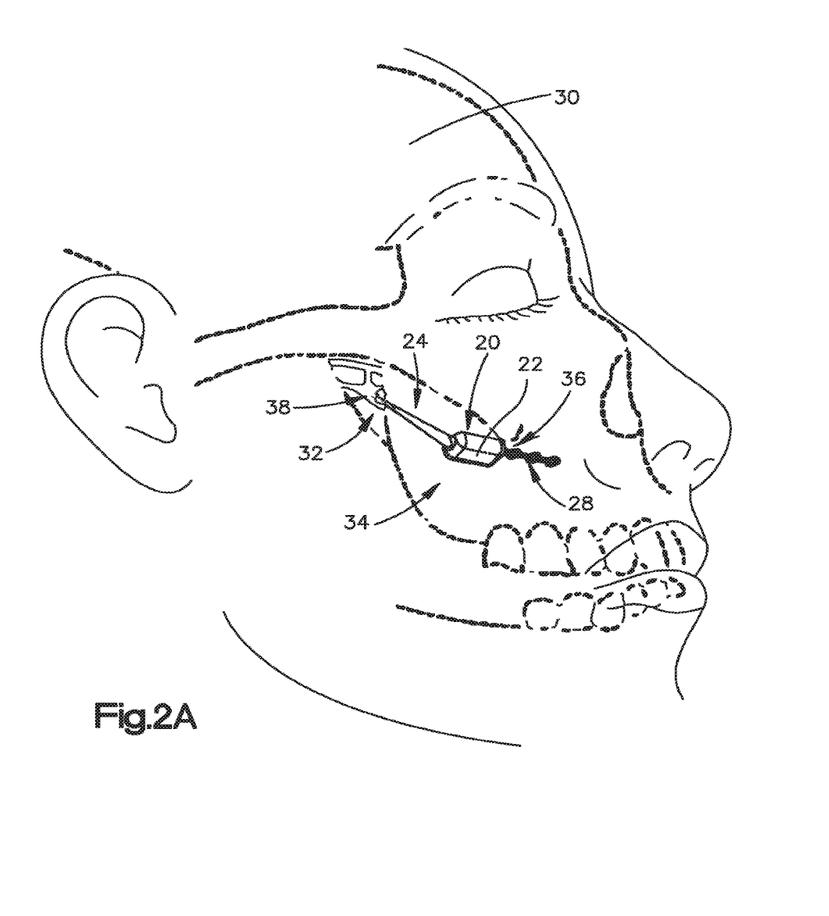
FIGS. 2A and 2B illustrate a portion of the system implanted in a patient.
Figure 2B:
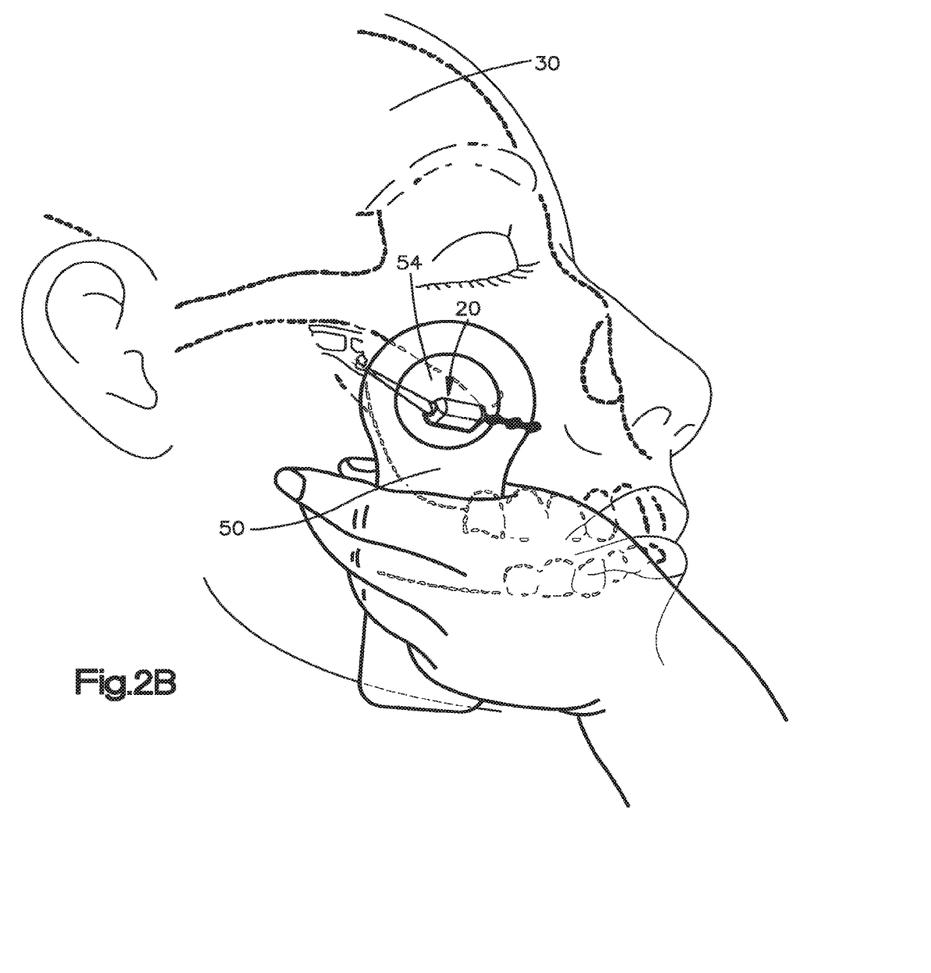

FIGS. 2A and 2B illustrate, by way of example, an implementation of the system 10 in which the IMD 20 is implanted in a patient in order to treat primary headaches, such as migraines, or other neurological disorders. As illustrated in FIG. 2A, the IMD 20 is implantable in a patient's head 30. In this particular implementation, the IMD 20 is implanted such that the stimulator body 22 is positioned medial to the zygoma 32 on the lateral/posterior maxilla 34 within the buccal fat pad of the cheek, and the integral fixation apparatus 28 is anchored to the zygomaticomaxillary buttress 36, such as by using standard craniomaxillofacial bone screws, for example. The stimulation lead 26 can be placed within the pterygopalatine fossa or, more specifically, in very close proximity to the sphenopalatine (pterygopalatine) ganglion (SPG) ganglion 38.

Referring to FIG. 2B, to operate the IMD 20, the patient manually positions the RC 50 adjacent his/her head 30 so that the antenna portion 54 is positioned in the proximity of the IMD 20. The patient can manipulate the position of the RC 50 in response to the indications provided by the feedback portion 220 to achieve a strong inductive link between the controller and the IMD 20.

Once a communication and power link is established via a feedback method, the IMD 20 administers the therapy in accordance with the instructions of the RC 50 and the stimulation parameters stored on the IMD. During use, the patient may be able to adjust certain stimulation parameters (amplitude, pulse width, frequency, combination thereof, or specific protocols with autonomic preset adjustment in two or more parameters at once) or parameters (ramp time, etc.) via the input device 62, e.g., by manipulating the control buttons 64. These adjustments are physician/clinician approved & configurable.

Figure 3:
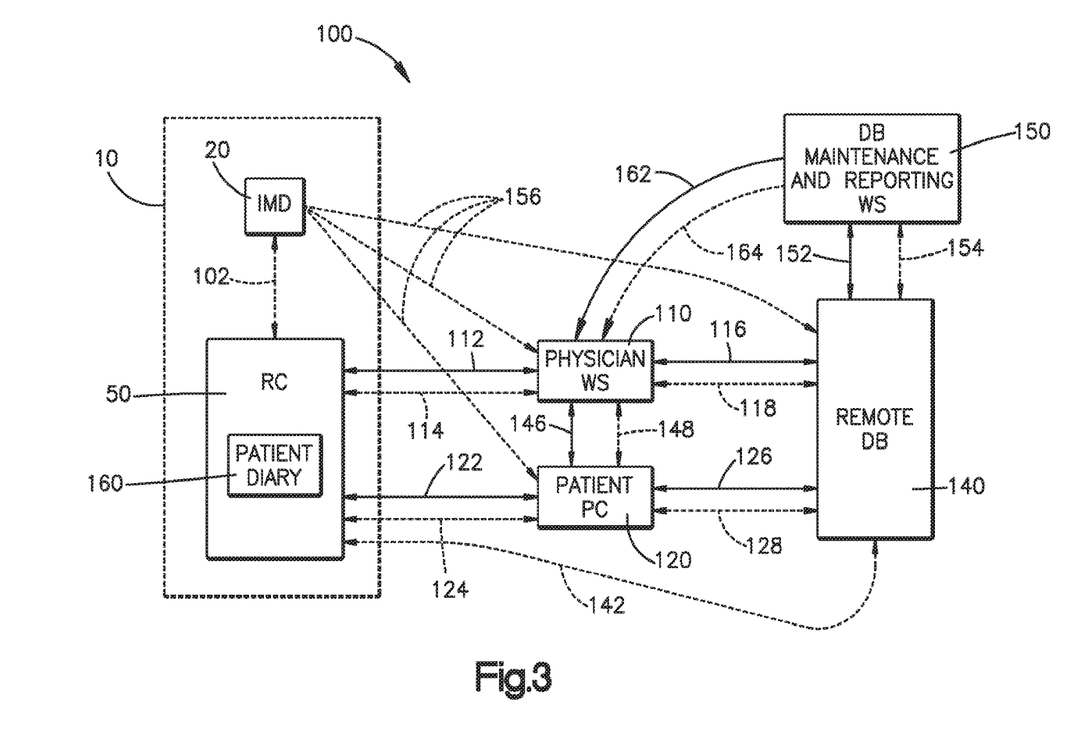
FIG. 3 is a schematic block diagram of the system for delivering therapy using an implantable medical device, according to the invention.

The RC 50 and IMD 20 are components of a system for applying stimulation therapy to a patient. Referring to FIG. 3, an example of a system 100 in which the RC 50 and IMD 20 are implemented includes multiple computer platforms, each of which may have a different remote location. These multiple platforms can be networked for communication with each other via a variety of wired (indicated in solid lines) and wireless (indicated in dashed lines) connections. The example system of FIG. 3 includes the medical device 10 (i.e., the IMD 20 and the RC 50), a physician workstation ("physician WS") 110, a patient personal computer/docking station ("patient PC") 120, and a remote database ("remote DB") 140.

The wireless communication/power connection between the RC 50 and the IMD 20 is illustrated in dashed lines at 102. This connection 102 may, for example, employ a medical implant specific communication protocol, such as a medical implant communication system (MICS) protocol. This specialized protocol helps institute a degree of safety and reliability in communications between the RC 50 and the IMD 20, especially while the IMD is implanted in the patient.

The physician WS 110, patient PC 120 (or cell phone, PDA, etc.), and remote DB 140 can be interconnected via a communication network 170 that includes wired connections (e.g., a wired internet connection), indicated generally with solid lines and wireless connections (e.g., a WiFi internet connection, a Bluetooth connection, or a GSM/CDMA/LTE mobile network connection), indicated generally with dashed lines. In the embodiment illustrated in FIG. 3, the physician WS 110 is has a wired connection 116 and a wireless connection 118 with the remote database 140. The patient PC 120 has a connected wired connection 126 and a wireless connection 128 with the remote database 140. The physician WS 110 and the patient PC 120 have a wired connection 146 and a wireless connection 148 with each other. The physician WS 110 and the database WS can also communicate with each other via a wired 162 or a wireless 164 connection. The physician WS 110, patient PC 120, remote DB 140, and database WS 150 can communicate with each other via the network 170 using any combination of the wired and wireless network connections.

The RC 50 can be connected to the physician WS 110 via a direct wired connection 112 (e.g., via a USB port or docking station), or via a wireless connection 114 (e.g., a WiFi connection, a Bluetooth connection, or a GSM/CDMA/LTE mobile network connection). Connected with the physician's WS 110, the RC 50 may act in a pass-through mode, allowing the physician to access the IMD 20 for programming or data retrieval via the physician WS. The RC 50 may indicate the occurrence of these events via the feedback portion 220. The feedback portion 220 may alert the patient to other occurrences, such as software updates, required diary entries, stimulation parameter changes, etc.

The RC 50 can also be connected to the patient personal computer 120 via a direct wired connection 122 (e.g., via the USB port or docking station), or via a wireless connection 124 (e.g., a WiFi connection, a Bluetooth connection, or a GSM/CDMA/LTE mobile network connection). The RC 50 may indicate this occurrence via the feedback portion 220, for example, by displaying a "PC Control" message on the display screen 60. The RC 50 can also communicate with the remote DB 140 via the network 170. Additionally, the RC 50 can be connected directly to the remote DB 140 via a wireless connection 142 (e.g., a GSM/CDMA/LTE mobile network connection).

From the above, those skilled in the art will appreciate that the system 100 has a highly selectable configuration, and that the communication between the RC 50, physician WS 110, patient PC 120, and remote DB 140 may be configured to occur in various combinations. In this configuration, the network 170 allows for the omission of certain portions or components of the system 100 and also for redundancy in various communication channels through the network.

For example, referring to FIG. 4A, in one communication configuration or mode, the RC 50 may communicate with the patient PC 120 via wireless connection 124, with the physician WS 110 via wired connection 112, and with the remote DB 140 via the wireless connection with the patient PC and either the wired 126 or wireless 128 connection between the patient PC and the remote DB.

In another example communication configuration or mode, referring to FIG. 4B, the RC 50 may communicate with the physician WS 110 and with the patient PC 120 via wired connections 112 and 122, respectively, and with the remote DB 140 via the wired connection 122 and either the wired connection 126 or wireless connection 128.

In yet another example communication configuration or mode, referring to FIG. 4C, the RC 50 may communicate with the physician WS 110 via the wired connection 112 and with the remote DB 140 directly via the wireless connection 142. In this configuration, the patient PC is not necessary to establish the necessary communication channels.

In a further example communication configuration or mode, referring to FIG. 4D, the RC 50 may communicate with the physician WS 110 via the wireless connection 114 and with the remote DB 140 directly via the wireless connection 142. Again, in this configuration, the patient PC is not necessary to establish the necessary communication channels.

Referring to FIG. 3, the system 100 also includes a database maintenance and reporting workstation ("database WS") 150 that is operatively connected to the remote DB 140 and/or the physician WS 110 via wired 152 or wireless 154 connections. The architecture in which the database WS 150 and the remote DB 140 are implemented can vary. For example, the database WS 150 may comprise a workstation on a local area network, and the remote DB 140 may be is stored on a server in that local area network. Alternatively, the remote DB 140 may be a cloud-based database that the RC 50, patient PC 120, physician WS 110, and database WS 150 access via the internet.

The system 100 also includes a patient diary 160 in which the patient records data associated with the treatments administered via the IMD 20. The data can be in the form of responses to questions asked by the system, and the questions can be either subjective or objective in nature. The questions can be prompted and answered both prior to, during, and/or after the therapy is applied. In this manner, answering the questions may serve as a gate to patient therapy by which therapy is denied until certain diary questions are answered. Post therapy diary questions can be answered immediately after the stimulation therapy is applied or sometime thereafter. The timing and content of the questions asked both pre and post therapy can be physician/clinician selected. Post therapy diary questions can be answered via the RC 50 directly or via the patient PC 120. The patient diary can be considered a portion of the therapy/clinical trial settings & data (Table 2).

The patient diary 160 is illustrated in FIG. 3 as being part of the RC 50 because this is where the data included in the diary is entered into the system 100 by the patient. The patient diary 160 may reside in a remote location or combination of locations. For example, the patient diary 160, while collected and entered at the RC 50, may be accumulated and stored at the remote DB 140 or at the physician WS 110. As another alternative, the patient diary 160 may comprise an internet based diary stored on a remote server and accessible via the internet. As a further alternative, the patient diary 160 may comprise a cloud based system in which the diary is accessible via the internet.

Once entered, when the RC 50 is operatively connected for communication with the system 100 (wired or wirelessly), the data from the patient diary 160 can be transmitted to the remote DB 140, to the physicians WS 120, to the patient PC 110, or to a cloud based storage system. Thereafter, the physician can access the data via the workstation 110. Additionally, the patient may also be able to access certain data from the patient diary 160, such as previously answered diary questions, unanswered diary questions or additional questions, via the patient PC 120. In an internet or cloud-based implementation, the patient can access the patient diary 160 online via web access. The feedback portion 220 may serve to provide feedback or indication (visual, audible, vibratory, etc.) regarding the diary entries. Such indications may, for example, include indications that questions require answering, questions are complete, etc.

The questions queried to the patient for entry in the patient diary 160 can be subjective questions or objective questions. Subjective questions can serve to help describe or categorize the headache episode in terms of symptoms, severity, duration, lasting effects, etc. The data from the subjective questions in the patient diary thus give patient specific details and sensory perceptions that can be used to evaluate and adjust the therapy regimen for that particular patient. Objective questions elicit from the patient factual details not subject to the patients perception, and thus generate data that can collected along with objective data from other patients and used to evaluate efficacy for the group as a whole. The subjective and objective data collected in the patient diary includes, but is not limited to, the data set forth below in Table 4:

TABLE 4

Patient Diary Data

| Subjective Data | Objective Data |
| --- | --- |
| Headache Pain Level | Headache Occurrence |
| Sensitivity to Light | Headache Start/End Time |
| Sensitivity to Sound | Acute Medication Usage |
| Aura Before | Rescue Medication Usage |
| Nausea/Vomiting | Medication Start Time |
| Throbbing/Pulsating Pain | Foods/Beverages Ingested Prior |
| Location (Side) - Left/Right/Both | Sleep Pattern |
| Activity/Movement Aleve Pain | Location - Work, Home, etc. |
| Stress Level | Activity - Reading, Computer, etc. |
| Tiredness | |
| Autonomic Symptoms | |

The questions for obtaining the patient diary data can be queried by the RC 50 at specific times or according to a predetermined schedule. For example, when the RC 50 is initially powered on, the patient may be prompted via any of the feedback modes to answer questions regarding headache pain levels, location (side) of the headache pain, acute medications taken, sensitivity to light/sound, the presence of nausea or vomiting, and the presence of autonomic symptoms (e.g., red/tearing eyes, blocked nose, eyelid swelling, etc.). When therapy is stopped, the patient may be prompted to answer questions regarding headache pain. At a predetermined time after therapy stops, such as one hour after therapy, the patient may be prompted to answer questions regarding headache pain levels, rescue medications taken, sensitivity to light/sound, the presence of nausea or vomiting, and the presence of autonomic symptoms.

Additionally, the therapy applied by the medical device 10 may be controlled or otherwise limited or scheduled according to a therapy cycle of a predetermined duration and which includes predetermined intervals according to which therapy is applied. As an example, a therapy cycle may be a 90 minute cycle during which therapy can be applied only during the first 15 minutes. Additionally, prior to beginning therapy, the therapy cycle may require that the headache diary questions be answered. The example therapy cycle may permit continuous or intermittent use during the initial 15 minutes of the 90 minute cycle, and the RC 50 will display the remaining therapy time during the initial 15 minutes of the therapy cycle. Once the 15 minute therapy time expires, no additional therapy is permitted for the remaining 75 minutes of the 90 minute therapy cycle. In applying scheduled therapy, any of the feedback modes can be used to alert the patient.

According to the invention, the system 100 can facilitate administering stimulation therapy as a part of an ongoing regimen in combating disorders, such as migraine headaches. At the patient level, the physician can program the IMD 20 via the workstation 110 to set the, individualized stimulation parameters, the individualized settings for the RC 50 (e.g., language, diary questions, screen settings, etc.), and any software/firmware updates that may be necessary. The RC 50 then can upload these items to the IMD 20. At home, the patient self-administers, within physician prescribed limits, the stimulation therapy on an as-needed basis, or in accordance with a schedule assigned by a physician/clinician.

The physician WS 110 is outfitted with software that allows the workstation to communicate with the RC 50 when connected thereto via either the wired connection 112 or the wireless connection 114. The physician WS 110 also may communicate with the RC 50 connected remotely to the patient PC 120, via the internet connection 146, 148. The physician WS 110, being additionally connected with the remote database 140, can also access the remote database as a central repository for information relating to patient data, stimulation settings, therapy settings, manufacturer notices, software/firmware updates, and other bulletins. Through the remote database 140, physicians/clinicians may receive stimulation parameters for loading onto an RC 50, which can then be downloaded to the IMD 20 via the RC 50.

The physician WS 110 can be a PC based system used by the physician to configure the IMDs 20 prior to implantation or post implantation. The programmer (physician) can interface with the RC 50 wirelessly or through the USB connection. In an embodiment, the RC 50 communicates with the physician WS 110 through the wired connection 112, and the controller may enter a pass-through mode in which all or some of the controls are disabled, leaving the controller to simply serves as a communication bridge between the physician WS 110 and the IMD 20. The RC 50 may also communicate with the physician WS wirelessly via the wireless connection 114. Through this communication, the programmer can instruct the RC 50 to communicate with the IMD 20, transmitting and receiving data via their built-in bi-directional telemetry capabilities. This allows the programming physician to, for example, install or update software/firmware and to set and adjust the stimulation parameters and therapy settings in the IMD 20.

The patient PC 110 can be a PC based system with installed proprietary software that provides for communicating with the RC 50 and relaying data to the remote DB 140. The patient PC 110 is not, however, limited to a PC based system. The system 100 can be adapted to provide for charging and communicating with the RC 50 in a variety of manners. For example, the system 100 may include a standalone charging/docking station with wireless internet communication capabilities for transmitting data to the remote DB 140. In this configuration, a PC is not necessary. As another example, the RC 50 could be fitted with a simple AC power cord for charging and short-range wireless communication capabilities (e.g., Bluetooth) for transmitting data to the remote DB 140 via an external device, such as a Bluetooth enabled PC or cell phone, or a PDA type device.

The remote DB 140 may be built on any platform that allows information to be stored, read, and updated. For example, the remote database can be an industry standard such as Oracle, Microsoft SQL Server, etc., that permits standard SQL (Structured Query Language) commands and queries to store, access, and manipulate the data contained therein. The remote DB 140 may also be an internet or web based (e.g., cloud based) platform for storing stimulation parameters (Table 1), Therapy Settings (Table 2), Therapy Session Data (Table 3) and patient diary data (Table 4). The remote DB 140 can additionally serve as a central repository for storing and distributing manufacturer notices/bulletins, instruction manuals and other materials, and software/firmware updates. The remote DB 140 can further serve as a central platform for administering a clinical trial. The remote DB 140 can include a table or tables that contain the serial numbers of all IMDs 20 that have been implanted in patients, and can also contain the therapy status of those patients.

For example, the database may include all the results of the clinical trial for all patients enrolled in the trial including, but not limited to, the patients' histories, therapy protocol for the patients, therapy efficacy, and treatment regimens for the patients and results to-date. To address privacy concerns, the data stored on the remote DB 140 may be blind to the identity of the patients. The remote DB 140 may, however, may store non-identifying clinically relevant patient data, such as height, weight, blood pressure, sex, and age of the clinical trial participants.

According to one aspect of the invention, the stimulation parameters and therapy settings programmed onto the IMD 20 can include all of the patient and device specific information necessary to perform the stimulation therapy on the patient. It is not necessary to include any patient or therapy specific data (e.g., stimulation parameters/therapy settings) on the RC 50 itself. Due to this, the RC 50 is necessary only to inductively power the IMD 20. This offers a great advantage in that any RC 50, whether it is the patient's personal unit, a physician's unit, or a replacement unit can be used to apply stimulation therapy via the IMD 20 without any pre-programming or set up. The RC 50 may thus be a turn-key unit ready to operate right out of the box.

As another advantage, the RC 50 can also perform its querying and recording functions without any preprogramming either. The RC 50 reads the patient diary questions and schedule from the IMD 20, administers the diary questions, and records the patient diary data accordingly. The RC 50 also reads and records the therapy session data and clinical trial data in real time during the therapy session. The RC 50 thus additionally initiate and administers the patient diary questions, records the therapy session data, and records the patient diary data without pre-programming any patient or trial specific parameters, settings, or data into the RC.

As a further advantage, storing the stimulation parameters and therapy settings on the IMD 20 helps ensure that the therapy will be applied according to the correct patient specific parameters and settings. This also helps ensure that the correct therapy type, patient language, and diary questions are applied/queried to the patient. All of these features advantageously improve the reliability and accuracy of the medical device 10 over a device that includes patient specific settings or parameters on the remote unit.

According to one aspect of the invention, the system 100, and the devices and methods implemented therein, enable a patient to respond to a therapy regimen. The stimulation therapy is applied as an ongoing treatment regimen tailored by the physician to treat the patient's specific medical condition. The system 100, the medical device 10, and the methods by which the stimulation therapy is applied enable the evaluation of the patient's response by the physician so that the efficacy of that particular patient's treatment regimen can be monitored, adjusted, and improved.

Figure 5:
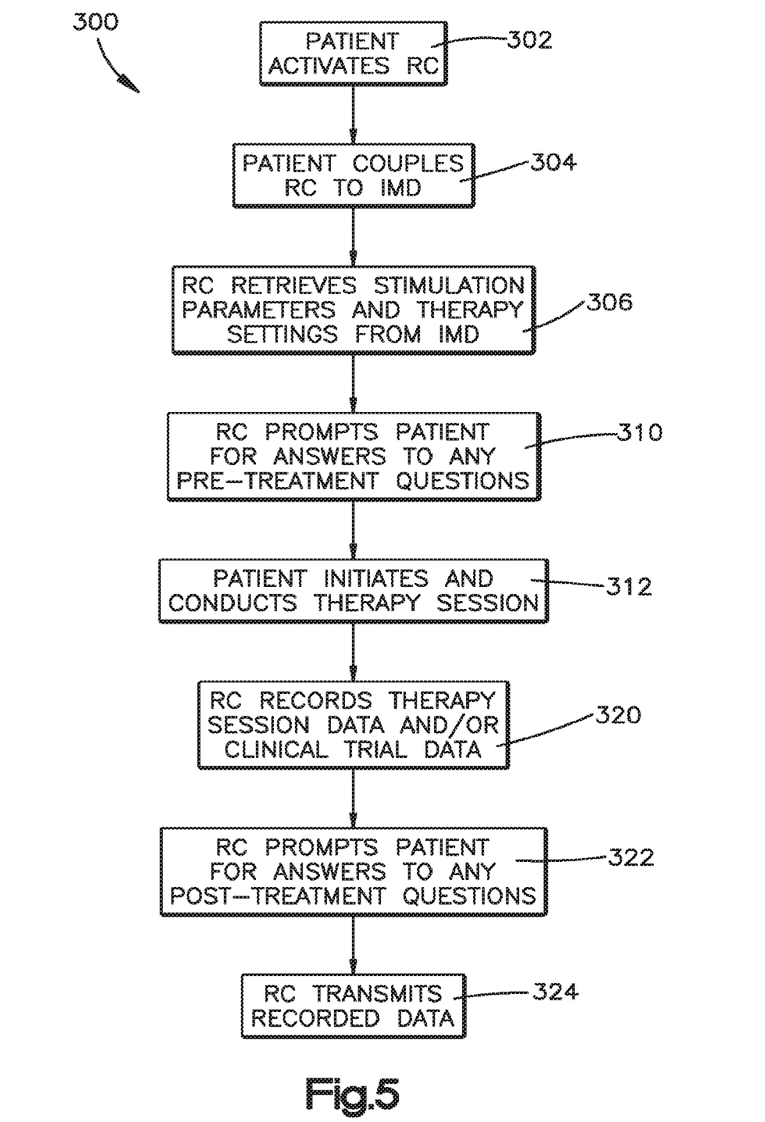

FIG. 5 illustrates a flowchart diagram of a process 300 by which therapy is applied using the medical device 10. The process 300 illustrated in FIG. 5 is an example of one process that may be used to apply therapy using the medical device 10. Those skilled in the art will appreciate that certain steps in the process may be adjusted, added, omitted, or performed in different order than that illustrated in the figures and described herein without departing from the spirit of the invention. For example, certain steps illustrated and described as being performed in a certain order may be performed simultaneously or in a different order, and certain steps illustrated and described as a single step may comprise multiple steps.

For example, an additional step could be implemented in which the application of therapy described in FIG. 5 may be predicated on gaining approval for using the medical device 10 to apply the therapy. Such approval requirements may be similar or identical to those described in U.S. patent application Ser. No. 12/688,524, filed Jan. 15, 2010, titled "APPROVAL PER USE IMPLANTED NEUROSTIMULATOR," the disclosure of which is hereby incorporated by reference in its entirety. As another example, in an initial use of an RC 50 with an IMD 20 where the RC has not previously communicated with that particular IMD, the RC may enter an initial mode where the RC prompts the patient (via any of the feedback modes) with an initial set of predetermined diary questions (e.g., a subset of those set forth in Table 4). Thereafter, the RC 50 will use the patient/clinical trial appropriate questions programmed on the IMD 20.

Referring to FIG. 5, when a patient senses the onset of an event, such as a migraine headache, the patient activates the RC 50, at step 302. The process 300 then proceeds to step 304, where the patient couples the RC 50 to the IMD 30. During coupling step 304, the RC 50 may provide feedback—audible, tactile, or both, that assists the patient in achieving the proper positioning of the RC 50 relative to the IMD 30. Once the RC 50 and IMD 30 are coupled, the process 300 proceeds to step 306, where the RC can retrieve stimulation parameters (Table 1) or therapy settings (Table 2). For example, at step 306, the RC 50 may retrieve patient diary questions to query the patient.

The process 300 then proceeds to step 310, where the RC 50 prompts, via any of the feedback modes, the patient for answers to any pre-treatment questions. These questions can be designed to elicit from the patient the patient diary data set forth in Table 4. This step 310 may be optional, as it is conditioned on whether the supervising physician/clinician has opted to require pre-treatment questions as a gateway to therapy. The process 300 then proceeds to step 312, where the patient initiates and conducts the therapy session. During the therapy session, if permitted by the supervising physician/clinician, the patient can adjust any adjustable parameters within the physician defined limits. The therapy session ends at step 314 due to either expiration of a timeout period or due to cessation by the patient.

The process 300 proceeds to step 320, where the RC 50 records the therapy session data (Table 3) and/or any necessary therapy settings (Table 2). The process 300 then proceeds to step 322, where the RC 50 prompts the patient for answers to any post-treatment questions, if the prompting for answers to such questions is enabled by the supervising physician/clinician. At step 342, the IMD 30 records the therapy session data. The process 300 proceeds to step 324, where the RC 50 transmits the recorded data, if this function is enabled. Alternatively, the recorded data may be stored until such a time that transmission of the data is convenient to the patient.

When the RC 50 transmits the recorded data to the remote database, the remote database updates its records and analyzes the data. The database can be utilized to compare the data to pre-programmed data and determines whether an appropriate party, e.g., the patient's physician or an administrator of the clinical trial, should be contacted. If so, the party is contacted and can take the appropriate action, as needed.

Figure 6:
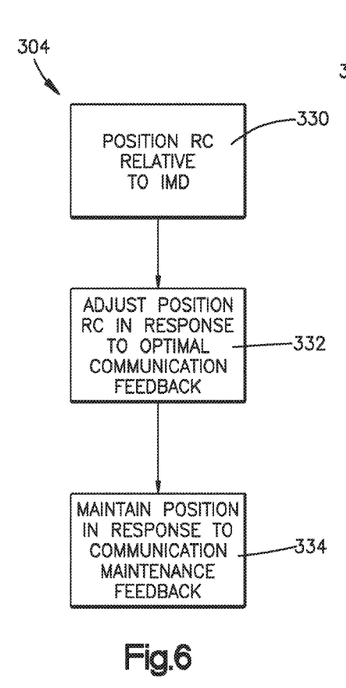

Referring to FIG. 6, according to the invention, the step 304 of coupling the RC 50 to the IMD 20 includes the initial step 330 of positioning the RC 50 relative to the IMD 20. In this step, the patient initially moves the RC 50 toward the position illustrated in FIG. 2B. Alternatively, the patient could bring the remote antenna coil 240 into the same or similar position. At step 332, the patient adjusts the position of the RC 50 (or remote coil 240) in response to the optimal communication feedback. As discussed above, the optimal communication feedback may comprise any of the various feedback modes of the feedback portion 220, alone or in combination. At step 334, the patient maintains the position of the RC 50 relative to the IMD 20 in response to the communication maintenance feedback. The communication maintenance feedback may comprise any of the various feedback modes of the feedback portion 220, alone or in combination.

Figure 7A:
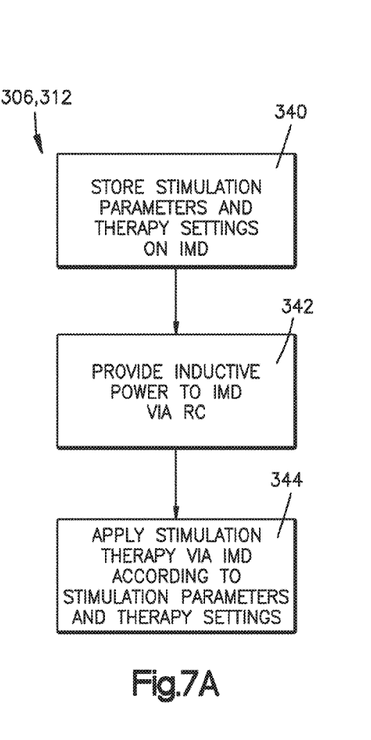

Referring to FIG. 7A, according to the invention, the steps 306, 312 include the initial step 340 of storing the stimulation parameters and therapy settings on the IMD 20. This can be done, as discussed above, via the physician WS 110. At step 342, the RC 50 provides inductive power to the IMD 20. At step 344, the IMD 20 applies stimulation therapy to the patient according to the stimulation parameters and therapy settings.

Advantageously, according to step 340, the stimulation parameters and therapy settings programmed onto the IMD 20 can include all of the patient and device specific information necessary to perform the stimulation therapy on the patient. The RC 50 does not require any patient or therapy specific data and is required only to inductively power the IMD 20.

Figure 7B:
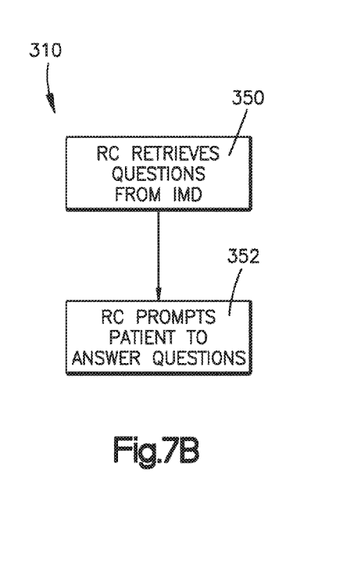

Referring to FIG. 7B, according to the invention, the step 310 includes the step 350 that the RC 50 retrieves questions from the IMD 20. At step 352, the RC 50 prompts the patient to answer the questions retrieved from the IMD 20. Advantageously, the RC 50 can thus perform its querying and recording functions without any patient specific preprogramming. The RC 50 reads the patient diary questions and schedule from the IMD 20, administers the diary questions, and records the patient diary data accordingly.

The processes illustrated in FIGS. 6, 7A, and 7B therefore offer the advantage in that as a further advantage, storing the stimulation parameters and therapy settings on the IMD 20 helps ensure that the therapy will be applied according to the correct patient specific parameters and settings. This also helps ensure that the correct therapy type, patient language, and diary questions are applied/queried to the patient. All of these features advantageously improve the reliability and accuracy of the medical device 10 over a device that includes patient specific settings or parameters on the remote unit.

From the above description of the invention, those skilled in the art will perceive improvements, changes and modifications. Such improvements, changes and modifications within the skill of the art are intended to be covered by the appended claims.

What is claimed is:

1. An apparatus for applying neurostimulation therapy to a patient, the apparatus comprising:
an implantable neurostimulator; and
a remote controller for inductively powering the neurostimulator and communicating with the neurostimulator,
wherein the neurostimulator is configured to apply stimulation therapy to the patient according to stimulation parameters and therapy settings, all of which are stored in the implanted neurostimulator, wherein the neurostimulator is configured to store therapy gateway questions and answers inputted by the patient as a gateway to receiving stimulation therapy from the implanted neurostimulator.

2. The apparatus recited in claim 1, wherein the implanted neurostimulator is configured to apply the stimulation therapy to the patient according to the stimulation parameters and therapy settings stored on the implanted stimulator without receiving any patient specific or therapy specific data from the remote controller.

3. The apparatus recited in claim 1, wherein the implanted stimulator is configured to store all therapy session data regarding the stimulation therapy applied by the implanted neurostimulator.

4. The apparatus recited in claim 1, wherein the remote controller can be used to inductively power the implanted neurostimulator to apply the stimulation therapy to the patient according to the stimulation parameters and therapy settings stored on the implanted stimulator without any pre-programming or set up.

5. The apparatus recited in claim 1, wherein the remote controller is configured to set and adjust stimulation parameters and therapy settings stored on the implanted neurostimulator.

6. The apparatus recited in claim 1, wherein the implanted neurostimulator is configured to stimulate a peripheral, central, or autonomic neural structure.

7. The apparatus recited in claim 1, wherein the implanted neurostimulator is configured to stimulate a sphenopalatine (pterygopalatine) ganglion (SPG).

8. The apparatus recited in claim 1, wherein the implanted neurostimulator is configured to stimulate a neural structure in order to treat a primary headache.

9. The apparatus recited in claim 1, wherein the stimulation parameters and therapy settings programmed onto the neurostimulator comprise all of the patient and device specific information necessary to apply the stimulation therapy.

10. The apparatus recited in claim 1, wherein the remote controller is configured to control operation of the implanted neurostimulator without receiving or requiring any patient specific data or therapy specific data and is required only to inductively power the implanted neurostimulator.

11. An apparatus for applying neurostimulation therapy to a patient, the apparatus comprising:
an implantable neurostimulator; and
a remote controller for inductively powering the neurostimulator and communicating with the neurostimulator,
wherein the neurostimulator is configured to apply stimulation therapy to the patient according to stimulation parameters and therapy settings, all of which are stored in the implanted neurostimulator, wherein the remote controller is configured to query the patient to answer questions as a gateway to receiving stimulation therapy from implanted neurostimulator, and wherein the remote controller is configured to receive the gateway questions from the implanted neurostimulator and to transmit answers inputted by the patient to the implanted neurostimulator, where the answers are stored.

12. The apparatus recited in claim 11, wherein the remote controller is configured to query the patient to answer questions after receiving stimulation therapy from the implanted neurostimulator.

13. The apparatus recited in claim 12, wherein the remote controller is configured to receive the post-stimulation questions from the implanted neurostimulator and to transmit answers inputted by the patient to the implanted neurostimulator, where the answers are stored.

14. An apparatus for applying neurostimulation therapy to a patient, the apparatus comprising:
   an implantable neurostimulator; and
   a remote controller for inductively powering the neurostimulator and communicating with the neurostimulator,
   wherein the neurostimulator is configured to apply stimulation therapy to the patient according to stimulation parameters and therapy settings, all of which are stored in the implanted neurostimulator, wherein the remote controller is programmed to query the patient to enter at least one of subjective and objective data regarding the patient's condition as a gateway to receiving stimulation therapy from implanted neurostimulator, and wherein both the queries and the data elicited from the patient by the queries are stored on the implanted neurostimulator.

15. The apparatus recited in claim 14, wherein the subjective data comprises at least one of headache pain level data, sensitivity to light data, sensitivity to sound data, aura before headache onset data, nausea data, vomiting data, throbbing pain data, pulsating pain data, pain location data, activity/movement effect on pain data, stress level prior to onset data, tiredness data, and autonomic symptoms data comprising at least one of red eyes, tearing eyes, blocked nose, and eyelid swelling data.

16. The apparatus recited in claim 14, wherein the objective data comprises at least one of headache occurrence data, headache start/end time data, acute medication usage data, rescue medication usage data, medication start time data, food/beverage ingestion prior to headache onset data, sleep pattern data, physical location at headache onset data, and activity prior to headache onset data.

17. An apparatus for applying neurostimulation therapy to a patient, the apparatus comprising:
   an implantable neurostimulator; and
   a remote controller for inductively powering the neurostimulator and communicating with the neurostimulator,
   wherein the neurostimulator is configured to apply stimulation therapy to the patient according to stimulation parameters and therapy settings, all of which are stored in the implanted neurostimulator, wherein the neurostimulator is the storage device for all patient specific stimulation parameters used to apply the stimulation therapy, all patient specific therapy settings that are used to apply the stimulation therapy, any gateway queries and data elicited from the gateway queries, and any post therapy queries and data elicited from the post therapy queries.

* * * * *